(12) United States Patent
Hicks et al.

(10) Patent No.: US 9,295,810 B2
(45) Date of Patent: Mar. 29, 2016

(54) PURIFICATION OF UNREFINED EDIBLE OILS AND FATS WITH MAGNESIUM SILICATE AND ORGANIC ACIDS

(71) Applicants: George E. Hicks, Elizabeth, IN (US); Brian S. Cooke, Sellersburg, IN (US); Bryan L. Bertram, Floyds Knobs, IN (US); Chris Abrams, Louisville, KY (US)

(72) Inventors: George E. Hicks, Elizabeth, IN (US); Brian S. Cooke, Sellersburg, IN (US); Bryan L. Bertram, Floyds Knobs, IN (US); Chris Abrams, Louisville, KY (US)

(73) Assignee: The Dallas Group of America, Inc., Whitehouse, NJ (US)

( * ) Notice: Subject to any disclaimer, the term of this patent is extended or adjusted under 35 U.S.C. 154(b) by 176 days.

(21) Appl. No.: 13/870,299

(22) Filed: Apr. 25, 2013

(65) Prior Publication Data
US 2013/0310588 A1    Nov. 21, 2013

Related U.S. Application Data

(60) Provisional application No. 61/638,527, filed on Apr. 26, 2012.

(51) Int. Cl.
| | | |
|---|---|---|
| *C11B 3/00* | (2006.01) |
| *A61M 25/01* | (2006.01) |
| *C11B 3/10* | (2006.01) |
| *C11B 3/04* | (2006.01) |
| *A61M 39/06* | (2006.01) |

(52) U.S. Cl.
CPC ............ *A61M 25/01* (2013.01); *A61M 39/0693* (2013.01); *C11B 3/001* (2013.01); *C11B 3/04* (2013.01); *C11B 3/10* (2013.01); *A61M 2025/0188* (2013.01); *A61M 2039/0626* (2013.01)

(58) Field of Classification Search
CPC .. A61M 25/01; A61M 39/0693; C11B 3/001; C11B 3/04; C11B 3/10
USPC ......................................................... 554/191
See application file for complete search history.

(56) References Cited

U.S. PATENT DOCUMENTS

| | | | |
|---|---|---|---|
| 4,629,588 A | 12/1986 | Welsh et al. | |
| 4,681,768 A * | 7/1987 | Mulflur et al. | ................ 426/417 |
| 4,734,226 A | 3/1988 | Parker et al. | |
| 4,781,864 A | 11/1988 | Pryor et al. | |
| 4,877,765 A | 10/1989 | Pryor et al. | |
| 4,880,574 A | 11/1989 | Welsh | |
| 4,939,115 A | 7/1990 | Parker et al. | |
| 5,006,356 A | 4/1991 | Munson | |
| 5,252,762 A | 10/1993 | Denton | |
| 5,298,638 A | 3/1994 | Toeneboehn et al. | |
| 5,597,600 A * | 1/1997 | Munson et al. | ............ 426/330.6 |
| 6,096,911 A | 8/2000 | Dralle-Voss et al. | |
| 6,346,286 B1 | 2/2002 | Council et al. | |
| 6,368,648 B1 | 4/2002 | Bertram et al. | |
| 6,638,551 B1 * | 10/2003 | Levy et al. | ................ 426/330.6 |
| 6,797,172 B2 | 9/2004 | Koseoglu et al. | |
| 7,635,398 B2 * | 12/2009 | Bertram et al. | ................. 44/605 |
| 7,867,538 B2 | 1/2011 | Binder et al. | |
| 2009/0199460 A1 | 8/2009 | Munson et al. | |
| 2010/0087666 A1 | 4/2010 | Munson et al. | |
| 2010/0233335 A1 | 9/2010 | Jalalpoor | |
| 2010/0324317 A1 | 12/2010 | Jalalpoor | |

* cited by examiner

*Primary Examiner* — Deborah D Carr
(74) *Attorney, Agent, or Firm* — Raymond J. Lillie

(57) ABSTRACT

The method of purifying an unrefined edible oil or fat by contacting the unrefined edible oil or fat with at least one adsorbent material. The at least one adsorbent material comprises magnesium silicate. The magnesium silicate may be used alone or in combination with other purifying materials, such as citric acid. Such method provides for improved removal of impurities, such as phosphorus-containing compounds, soap, chlorophyll, metals, and sterol glucosides from the unrefined edible oil or fat.

52 Claims, No Drawings

PURIFICATION OF UNREFINED EDIBLE OILS AND FATS WITH MAGNESIUM SILICATE AND ORGANIC ACIDS

This application claims priority based on provisional application Ser. No. 61/638,527, filed Apr. 26, 2012, the contents of which are incorporated by reference in their entirety.

This invention relates to the purification of unrefined edible oils and fats, such as cooking oils and fats, for example. More particularly, this invention relates to the purification of an unrefined edible oil or fat by contacting the unrefined oil or fat with at least one adsorbent material comprising magnesium silicate, either alone or in combination with other purifying materials, such as citric acid or malic acid, for example.

Edible oils and fats, such as cooking oils and fats, for example, need to be refined and processed in order to remove impurities before they can be used in cooking or before they can be consumed. Impurities that must be removed include free fatty acids, phosphorus compounds, such as phosphorus gums, soap, metals, chlorophyll, water, and other impurities.

Free fatty acids may be removed from the unrefined edible oil or fat by chemical or physical means. In a chemical refining process, a caustic solution, such as sodium hydroxide, is added to the oil or fat in order to convert free fatty acids into a corresponding soap molecule, such as sodium oleate. In a physical refining process, the oil or fat is subjected to steam distillation that strips free fatty acids from the oil or fat.

For further refining and processing of the oil or fat, a water wash and/or adsorbent treatment is (are) used to remove soaps and phosphorus compounds such as phosphorus gums, for example, as well as sterol glucosides. The oil or fat also may be deodorized to remove trace amounts of free fatty acids, color bodies, and odors.

Silicas have been used as an adsorbent for removing impurities from unrefined edible oils. Examples of silicas which have been used to purify unrefined edible oils are described in U.S. Pat. Nos. 4,629,588; 4,734,226; 4,782,864; 4,877,765; 4,880,574; 4,939,115; 5,298,638; and 7,867,538, and U.S. published Patent Application No. US 2010/0233335. U.S. Pat. No. 6,346,246 discloses treating unrefined edible oils with a sorbent produced by mixing a clay with a dry granular organic acid. U.S. published Patent Application No. US2010/0324317 discloses treating an unrefined edible oil with metal oxide sols or silica sols.

Applicants have discovered that if an unrefined edible oil or fat is contacted with magnesium silicate, either alone or in combination with other purifying materials, there is improved removal of impurities, including phosphorus-containing compounds and chlorophyll, as well as entrained water, from the edible oil or fat.

Thus, in accordance with an aspect of the present invention, there is provided a method of purifying an unrefined edible oil or fat. The method comprises contacting the unrefined edible oil or fat with at least one adsorbent material. The at least one adsorbent material comprises magnesium silicate.

The term "unrefined edible oil or fat," as used herein, means an oil or fat that includes impurities that should be removed from the oil or fat in order to provide an oil or fat that is suitable for cooking or consumption. The term includes oils and fats that have not been subjected to any refining, as well as oils and fats which have been subjected to some refining, but from which all impurities have not been removed. For example, the term includes an oil or fat that has been treated to remove or neutralize free fatty acids, but has not been treated to remove other impurities such as soaps, phosphorus compounds (such as phosphorus gums), chlorophyll, metals, sterol glucosides, color bodies, and/or odors. The term "edible oil or fat", as used herein, means any animal or vegetable oil or fat that has been refined properly and is suitable for cooking or consumption. Such fats and oils include, but are not limited to, beef tallow, pork lard, soybean oil, canola oil, rapeseed oil, corn oil, sunflower oil, coconut oil, safflower oil, and peanut oil.

In one non-limiting embodiment, the magnesium silicate has the following properties:

| | |
|---|---|
| Loss on Ignition | 15% max (dry basis) |
| % MgO | 15% min. (ignited basis) |
| % $SiO_2$ | 67% min. (ignited basis) |
| Soluble salts | 3% max. |
| Mole ratio $MgO:SiO_2$ | 1:1.36 to 1:3.82 |

In another non-limiting embodiment, the magnesium silicate is an amorphous, hydrated, precipitated, synthetic magnesium silicate having a surface area of at least 300 square meters per gram. In another non-limiting embodiment, the magnesium silicate has a surface area from about 400 square meters per gram to about 700 square meters per gram. In yet another non-limiting embodiment, the magnesium silicate has a surface area from about 400 square meters per gram to about 600 square meters per gram. In addition, such magnesium silicate may be employed as coarse particles, with at least 75%, and preferably at least 85% of the particles having a particle size which is greater than 400 mesh, and with no more than 15%, and preferably no more than 5%, all by weight, having a particle size greater than 40 mesh. In most cases, the average particle size of the magnesium silicate employed in accordance with the present invention is in the order of but not limited to 20-175 microns. It is to be understood, however, that the magnesium silicate may have a particle size different than the sizes mentioned hereinabove.

In addition, the amorphous, hydrated, precipitated magnesium silicate which is employed in accordance with a non-limiting embodiment of the present invention generally has a bulk density in the order of from 15-35 lbs./cu. ft., a pH of 3-10.8 (5% water suspension) and a mole ratio of MgO to $SiO_2$ of 1:1.0 to 1:4.0.

The following is a specification and typical value for a magnesium silicate which is employed in accordance with a non-limiting embodiment of the present invention.

| Parameter | Specification | Typical Value |
|---|---|---|
| Loss on Ignition at 900° C. | 15% max. | 12% |
| Mole Ratio $MgO:SiO_2$ | 1:2.25 to 1:2.75 | 1:2.60 |
| pH of 5% Water Suspension | 9.5 ± 0.5 | 9.8 |
| Soluble Salts % by wt. | 3.0 max. | 1.0% |
| Average Size, Microns | | 55 |
| Surface Area (B.E.T.) | 300 $M^2$/g (min.) | 400 |
| Refractive Index | | Approx. 1.5 |

A representative example of such an amorphous, hydrated, precipitated synthetic magnesium silicate having a surface area of at least 300 square meters per gram is available as Magnesol® Polysorb 30/40, a product of the Dallas Group of America, Inc., Whitehouse, N.J., and also is described in U.S. Pat. No. 4,681,768.

In another non-limiting embodiment, the magnesium silicate is a magnesium silicate which has a surface area of no more than 150 square meters per gram. In another non-limiting embodiment, the magnesium silicate has a surface area from about 50 square meters per gram to about 150 square meters per gram. In a non-limiting embodiment, the magnesium silicate has a surface area such a magnesium silicate has a mole ratio of MgO to $SiO_2$ of from about 1:3.0 to about 1:3.8, and a pH (5% water suspension) of from about 9.5 to about 10.5. An example of such a magnesium silicate is available as Magnesol® HMR-LS, a product of the Dallas Group of America, Inc., Whitehouse, N.J.

In another non-limiting embodiment, the magnesium silicate is an amorphous, hydrous, precipitated synthetic magnesium silicate, which has a pH less than about 9.0. As used herein, the term "precipitated" means that the amorphous hydrated precipitated synthetic magnesium silicate is produced as a result of precipitation formed upon the contact of a magnesium salt and a source of silicate in an aqueous medium.

For purposes of the present invention, the pH of the magnesium silicate is the pH of the magnesium silicate as measured in a 5% slurry of the magnesium silicate in water. The pH of the magnesium silicate in a 5% slurry may be from about 8.2 to about 8.9, and more preferably from about 8.5 to about 8.8, and most preferably is about 8.5. Examples of such amorphous hydrous precipitated synthetic magnesium silicates are described in U.S. Pat. No. 5,006,356, and also are available as Magnesol® R30 and Magnesol® R60, products of the Dallas Group of America, Inc., Whitehouse, N.J. Magnesol® R30 has an average particle size of 30 microns, and Magnesol® R60 has an average particle size of 60 microns.

In a further non-limiting embodiment, the magnesium silicate has a pH (5% water suspension) of from about 9.0 to about 9.5. In another non-limiting embodiment, the magnesium silicate may be in the form of talc.

It is to be understood, however, that the scope of the present invention is not to be limited to any specific type of magnesium silicate or method for the production thereof.

In general, the unrefined edible oil or fat is contacted with the magnesium silicate in an amount effective to remove impurities from the unrefined edible oil or fat. In a non-limiting embodiment, the unrefined edible oil or fat is contacted with the magnesium silicate in an amount of from about 0.01 wt. % to about 5.0 wt. %, based on the weight of the unrefined edible oil or fat. In another non-limiting embodiment, the unrefined edible oil or fat is contacted with the magnesium silicate in an amount of from about 0.05 wt. % to about 1.0 wt. %, based on the weight of the unrefined edible oil or fat.

The unrefined edible oil or fat is contacted with the magnesium silicate in an amount effective to remove impurities therefrom. Impurities which may be removed include, but are not limited to, phosphorus-containing compounds, including phosphorus gums, soap, metals (such as, but not limited to, sodium, potassium, magnesium, calcium, iron, aluminum, and lead), chlorophyll, water, and free fatty acids.

The treatment of the unrefined edible oil with magnesium silicate as hereinabove described provides an edible oil which meets accepted standards for the trade and transportation of edible oils, including cooking oils. Such standards include those of the National Institute of Oilseed Products (NIOP), the American Oil Chemists Society, and the ISO.

In another non-limiting embodiment, the at least one adsorbent material, in addition to magnesium silicate, may include additional adsorbent materials such as, for example, bleaching clays.

In a non-limiting embodiment, the unrefined edible oil or fat is contacted with magnesium silicate and at least one other agent for purifying edible oils and fats. In another non-limiting embodiment, the at least one other agent for purifying the unrefined edible oil or fat is at least one organic acid.

Thus, in accordance with another aspect of the present invention, there is provided a method of purifying an unrefined edible oil or fat by contacting the unrefined edible oil or fat with (i) at least one adsorbent material comprising magnesium silicate and (ii) at least one organic acid.

The magnesium silicate may, in non-limiting embodiments, be selected from those hereinabove described, and the unrefined edible oil or fat may be contacted with the magnesium silicate in amounts as hereinabove described.

The unrefined edible oil or fat may be contacted with the at least one organic acid prior to, concurrently with, or subsequent to contacting the unrefined edible oil or fat with the magnesium silicate.

In a non-limiting embodiment, the unrefined edible oil or fat is contacted with the at least one organic acid prior to contacting the unrefined edible oil or fat with the magnesium silicate.

In another non-limiting embodiment, the at least one edible oil or fat is contacted with the at least one organic acid concurrently with the magnesium silicate.

In another non-limiting embodiment, the unrefined edible oil or fat is contacted with at least one organic acid subsequent to contacting the unrefined edible oil or fat with magnesium silicate.

In a non-limiting embodiment, the at least one organic acid is selected from the group consisting of citric acid, malic acid, and mixtures thereof. In another non-limiting embodiment, the at least one organic acid is citric acid. In yet another non-limiting embodiment, the at least one organic acid is malic acid.

The at least one organic acid may be in the form of a solution or may be a solid, such as a powder, for example.

In a non-limiting embodiment, the at least one organic acid is in the form of an aqueous solution. In another non-limiting embodiment, the at least one organic acid is present in the aqueous solution in an amount of from about 10% to about 80% by weight. In yet another non-limiting embodiment, the at least one organic acid is present in the aqueous solution in an amount of about 50% by weight.

In a non-limiting embodiment, the unrefined edible oil or fat is contacted with the aqueous solution of the at least one organic acid in an amount of from about 0.01 wt. % to about 5.0 wt. %, based on the weight of the unrefined edible oil or fat. In another non-limiting embodiment, the unrefined edible oil or fat is contacted with the aqueous solution of the at least one organic acid in an amount of from 0.5 wt. % to about 4.0 wt. %, based on the weight of the unrefined edible oil or fat.

In another non-limiting embodiment, the at least one organic acid is in the form of a solid, such as a solid powder. In a non-limiting embodiment, the unrefined edible oil or fat is contacted with a solid powder of the at least one organic acid in an amount of from about 0.01 wt. % to about 5.0 wt. %, based on the weight of the unrefined edible oil or fat. In another non-limiting embodiment, the unrefined edible oil or fat is contacted with a solid powder of the at least one organic acid in an amount of from about 0.5 wt. % to about 4.0 wt. %, based on the weight of the unrefined edible oil or fat.

The invention now will be described with respect to the following examples; however, the scope of the present invention is not intended to be limited thereby.

The invention now will be described with respect to the following examples. It is to be understood, however, that the scope of the present invention is not intended to be limited thereby.

EXAMPLE 1

Magnesium silicate was evaluated, either alone or in combination with bleaching clay for the removal of soap from a once refined soybean oil, or ORSO. The magnesium silicate had a pH of 8.60, an average particle size of 64 microns, a surface area of 519 square meters per gram, and a molar ratio of magnesium oxide to silicon dioxide of 1:2.65. The magnesium silicate was allowed to mix with the ORSO at a temperature of 225° F. (107° C.) for 20 minutes before filtering. The results are shown in Table 1 below.

TABLE 1

| Adsorbent | ppm soap |
| --- | --- |
| Crude ORSO (control) | 24 |
| 0.05 wt. % magnesium silicate/ 0.25 wt. % bleaching clay | 4 |
| 0.15 wt. % magnesium silicate | 4 |

The above results show that magnesium silicate, either alone or in combination with bleaching clay, reduced soap by 83.3% in both cases.

EXAMPLE 2

ORSO was contacted with the magnesium silicate described in Example 1 in an amount of 0.25 wt. %, based on the weight of the ORSO, for 20 minutes at a temperature of 225° F. (107° C.), and the magnesium silicate was evaluated for the removal of soap, water, and metals from the ORSO. The results are shown in Table 2 below.

TABLE 2

| Adsorbent | Soap (ppm) | Water (ppm) | Al (ppm) | Pb (ppm) | Na (ppm) | Ca (ppm) | Mg (ppm) | P (ppm) | K (ppm) |
| --- | --- | --- | --- | --- | --- | --- | --- | --- | --- |
| Crude ORSO (control) | 472 | 7,443 | 4 | 2 | 24 | 0 | 5 | 18 | 17 |
| 0.25 wt. % magnesium silicate | 0 | 422 | 3 | 1 | 4 | 0 | 1 | 11 | 10 |

The above results show that magnesium silicate was effective and reducing soap, water, and all metals present and measured in the ORSO.

EXAMPLE 3

ORSO was contacted with the magnesium silicate of Example 1 in an amount of 0.25 wt. %, based on the weight of the ORSO, for 20 minutes at a temperature of 225° F. (107° C.), and the magnesium silicate was evaluated for the removal of sterol glucosides and chlorophyll from the ORSO. The results are shown in Table 3 below.

TABLE 3

| Adsorbent | Total Sterol Glucosides (ppm) | Chlorophyll A (ppm) | Chlorophyll B (ppm) |
| --- | --- | --- | --- |
| Crude ORSO (control) | 24.6 | 1.116 | 0 |
| 0.25 wt. % magnesium silicate | 9.6 | 1.069 | 0 |

The above results show that the magnesium silicate was effective in reducing sterol glucosides and some chlorophyll from the ORSO.

EXAMPLE 4

Crude ORSO was contacted with 0.3 wt. % silica gel or 0.3% wt. % of the magnesium silicate of Example 1 at 100° C. for 20 minutes. The magnesium silicate and silica gel were evaluated for the removal of soaps, water, and metals from the ORSO. The results are shown in Table 4 below.

TABLE 4

| Adsorbent | Temp (° C.) | Time (min) | Soap (ppm) | Water (ppm) | Ca (ppm) | K (ppm) | Mg (ppm) | Na (ppm) | P (ppm) |
|---|---|---|---|---|---|---|---|---|---|
| Crude ORSO (control) | | | 272 | 4894 | 0.8 | 0.6 | 0.2 | 4.5 | 1.6 |
| 0.3% Silica Gel | 100 | 20 | 131 | 3325 | 0.4 | 0.2 | <0.1 | 1.6 | 0.7 |
| 0.3% Magnesium Silicate | 100 | 20 | 23 | 1897 | 0.4 | 0.1 | <0.1 | 0.9 | 0.1 |

The above results show that magnesium silicate was more effective than silica gel in removing soaps, water, and metals from the ORSO.

EXAMPLE 5

Crude ORSO was contacted with 0.3 wt. % silica gel or 0.3 wt. % of the magnesium silicate of Example 1 at 100° C. for 20 minutes. The magnesium silicate and silica gel were evaluated for the removal of sterol glucosides from the ORSO. The results are shown in Table 5 below.

TABLE 5

| Adsorbent | Temp (° C.) | Time (min) | Total Sterol Glucosides (ppm) |
|---|---|---|---|
| Crude ORSO (control) | | | 490 |
| 0.3% Silica Gel | 100 | 20 | 120 |
| 0.3% Magnesium Silicate | 100 | 20 | 80 |

The above results show that magnesium silicate was more effective than silica gel in removing sterol glucosides from the ORSO.

EXAMPLE 6

Once refined corn oil was contacted with 0.75 wt. % of the magnesium silicate of Example 1 at 180° F. for 10 minutes, or was contacted with 0.5 wt. % or 0.75 wt. % of a 50% by weight aqueous solution of citric acid at 180° F. for 5 minutes, after which 0.5 wt. % or 0.75 wt. % of the magnesium silicate of Example 1 was mixed with the once refined corn oil and citric acid for 10 minutes. The magnesium silicate, and the combination of citric acid and magnesium silicate, were evaluated for the removal of soap, phosphorus, and sulfur from the once refined corn oil. The results are shown in Table 6 below.

TABLE 6

| Sample ID | Treatment % | Soap (ppm) | % Reduction | P (ppm) | % Reduction | S (ppm) | % Reduction |
|---|---|---|---|---|---|---|---|
| Initial Oil | | 233 | | 14 | | 37 | |
| Magnesium Silicate | 0.75% | 117 | 49.79% | 10 | 28.57% | 31 | 16.22% |
| 50% Citric Acid Solution/Magnesium Silicate | 0.5%/0.75% | 5 | 97.85% | 1 | 92.86% | 25 | 32.43% |
| 50% Citric Acid Solution/Magnesium Silicate | 0.75%/0.75% | 22 | 90.56% | 0.5 | 96.43%. | 28 | 24.32% |
| 50% Citric Acid Solution/Magnesium Silicate | 0.5%/0.5% | 20 | 91.42% | 3 | 78.57% | 29 | 21.62% |
| 50% Citric Acid Solution/Magnesium Silicate | 0.75%/0.75% | 0 | 100.00% | 2 | 85.71% | 28 | 24.32% |

The above results show that there was improved removal of soap, phosphorus, and sulfur with a combination of magnesium silicate and citric acid than with magnesium silicate alone.

EXAMPLE 7

Once refined corn oil was contacted with 2 wt. % of the magnesium silicate of Example 1 at 180° F. for 10 minutes, or was contacted with 2 wt. % of a 50% aqueous solution of citric acid for 5 minutes, after which 2 wt. % of the magnesium silicate of Example 1 was added to the once refined corn oil and citric acid, and was mixed with the once refined corn oil and citric acid for 10 minutes. The magnesium silicate, and the combination of citric acid and magnesium silicate, were evaluated for removal of soap, sulfur, sodium, phosphorus, and potassium from the once refined corn oil. The results are given in Table 7 below.

TABLE 7

| | Treatment % | Soap (ppm) | % Reduction | S (ppm) | % Reduction | Na (ppm) | % Reduction | P (ppm) | % Reduction | K (ppm) | % Reduction |
|---|---|---|---|---|---|---|---|---|---|---|---|
| Initial Oil | | 643 | | 38 | | 51 | | 177 | | 67 | |
| Magnesium Silicate | 2.0% | 487 | 24.3% | 23 | 39.5% | 46 | 9.8% | 63 | 64.4% | 8 | 88.1% |
| 50% Citric Acid Solution/ Magnesium Silicate | 2.0%/2.0% | 60 | 90.7% | 21 | 44.7% | 6 | 88.2% | 5 | 97.2% | 2 | 97.0% |

The above results show that the combination of citric acid and magneuim silicate provided for improved removal of the above-mentioned impurities than magnesium silicate alone.

EXAMPLE 8

Once refined corn oil was treated according to one of the following:

(i) contact with 2 wt. % of the magnesium silicate of Example 1 at 180° F. for 10 minutes (ii) contact with 2 wt. % of a 50% aqueous solution of citric acid at 180° F. for 5 minutes, after which 2 wt. % of the magnesium silicate of Example 1 was mixed with the once refined corn oil and citric acid solution for 10 minutes.

(iii) contact with 1 wt. % citric acid powder at 180° F. for 5 minutes, after which 2 wt. % of the magnesium silicate of Example 1 was mixed with the once refined corn oil and citric acid powder for 10 minutes.

The magnesium silicate and combinations of citric acid and magnesium silicate were evaluated for removal of free fatty acids (FFA) and soap. The results are shown in Table 8 below.

TABLE 8

| | Treatment % | Soap (ppm) | % Reduction |
|---|---|---|---|
| Initial Oil | | 707 | |
| Magnesium Silicate | 2.0% | 532 | 24.8% |
| 50% Citric Acid Solution/ Magnesium Silicate | 2.0%/2.0% | 43 | 93.9% |
| Citric Acid Powder/ Magnesium Silicate | 1.0%/2.0% | 245 | 65.3% |

The above results show that the combinations of magnesium silicate and citric acid provided for improved removal of soap than magnesium silicate alone.

EXAMPLE 9

Once refined corn oil was treated according to one of the following:

(i) contact with 2 wt. % of the magnesium silicate of Example 1 at 180° F. for 10 minutes;

(ii) contact with 2 wt. % of a 50% aqueous solution of citric acid at 180° F. for 5 minutes, after which 2 wt. % of the magnesium silicate of Example 1 was mixed with the once refined corn oil and citric acid for 10 minutes;

(iii) contact with 4 wt. % of a 50% aqueous solution of citric acid at 180° F. for 5 minutes, after which 2 wt. % of the magnesium silicate of Example 1 was mixed with the once refined corn oil and citric acid for 10 minutes (iv) contact with 2.0 wt. % of a 50% aqueous solution of malic acid at 180° F. for 5 minutes, after which 2 wt. % of the magnesium silicate of Example 1 was mixed with the once refined corn oil and malic acid for 10 minutes;

(v) contact with a mixture of 1 wt. % citric acid powder, 2 wt. % of the magnesium silicate of Example 1, and 1 wt. % water at 180° F. for 10 minutes.

The magnesium silicate and combinations of magnesium silicate and citric acid or malic acid were evaluated for removal of soap, sulfur, iron, sodium, calcium, phosphorus, and potassium. The results are shown in Table 9 below.

TABLE 9

| | Treatment % | Soap (ppm) | % Reduction | S (ppm) | % Reduction | Fe (ppm) | % Reduction |
|---|---|---|---|---|---|---|---|
| Initial Oil | | 652 | | 50 | | 13 | |
| Magnesium Silicate | 2.00% | 635 | 2.6% | 24 | 52.0% | 2 | 84.6% |
| 50% Citric Acid Solution/Magnesium Silicate | 2.0%/2.0% | 0 | 100.0% | 24 | 52.0% | 0 | 100.0% |
| 50% Citric Acid Solution/Magnesium Silicate | 4.0%/2.0% | 0 | 100.0% | 24 | 52.0% | 0 | 100.0% |
| 50% Malic Acid Solution/Magnesium Silicate | 2.0%/2.0% | 0 | 100.0% | 22 | 56.0% | 0 | 100.0% |
| Dry Citric/ Magnesium Silicate/Water together | 1.0%/2.0%/1.0% | 0 | 100.0% | 26 | 48.0% | 2 | 84.6% |

TABLE 9-continued

|  | Na (ppm) | % Reduction | Ca (ppm) | % Reduction | P (ppm) | % Reduction | K (ppm) | % Reduction |
|---|---|---|---|---|---|---|---|---|
| Initial Oil | 83 |  | 53 |  | 347 |  | 56 |  |
| Magnesium Silicate | 59 | 28.9% | 16 | 69.8% | 100 | 71.2% | 4 | 92.9% |
| 50% Citric Acid Solution/Magnesium Silicate | 7 | 91.6% | 0 | 100.0% | 14 | 96.0% | 0 | 100.0% |
| 50% Citric Acid Solution/Magnesium Silicate | 2 | 97.6% | 0 | 100.0% | 18 | 94.8% | 0 | 100.0% |
| 50% Malic Acid Solution/Magnesium Silicate | 2 | 97.6% | 0 | 100.0% | 18 | 94.8% | 0 | 100.0% |
| Dry Citric/ Magnesium Silicate/Water together | 14 | 83.1% | 4 | 92.5% | 81 | 76.7% | 3 | 94.6% |

The above results show that the combinations of magnesium silicate with citric acid or malic acid provide for improved removal of the above-identified impurities than magnesium silicate alone.

The disclosures of all patents and publications (including published patent applications) are hereby incorporated by reference to the same extent as if each patent and publication were incorporated individually by reference.

It is to be understood, however, that the scope of the present invention is not to be limited to the specific embodiments described above. The invention may be practiced other than as particularly described and still be within the scope of the accompanying claims.

What is claimed is:

1. A method of purifying an unrefined edible oil or fat, comprising:
   contacting said unrefined edible oil or fat with at least one adsorbent material, wherein said at least one adsorbent material comprises magnesium silicate.

2. The method of claim 1 wherein said magnesium silicate has a surface area of at least 300 square meters per gram.

3. The method of claim 2 wherein said magnesium silicate has a surface area of at least 400 to about 700 square meters per gram.

4. The method of claim 2 wherein said magnesium silicate has a particle size of from about 20 microns to about 175 microns.

5. The method of claim 2 wherein said magnesium silicate has a bulk density of from about 15 to about 35 pounds per cubic foot.

6. The method of claim 1 wherein said magnesium silicate is an amorphous hydrous precipitated synthetic magnesium silicate, said magnesium silicate having been treated to reduce the pH thereof to less than about 9.0.

7. The method of claim 6 wherein said magnesium silicate has a pH in a 5% slurry of from about 8.2 to about 8.9.

8. The method of claim 7 wherein said magnesium silicate has a pH in a 5% slurry of from 8.5 about to about 8.8.

9. The method of claim 1 wherein said magnesium silicate has a surface area of no more than 150 square meters per gram.

10. The method of claim 9 wherein said magnesium silicate has a surface area of no more than 50 square meters per gram to about 150 square meters per gram.

11. The method of claim 10 wherein said magnesium silicate has a mole ratio of MgO to $SiO_2$ of from about 1:3.0 to about 1:3.8 and a pH in a 5% water suspension of from about 9.5 to about 10.5.

12. The method of claim 1 wherein said magnesium silicate has a pH of from about 9.0 to about 9.5.

13. The method of claim 1 wherein said unrefined edible oil or fat is contacted with said magnesium silicate in an amount of from about 0.01 wt. % to about 5.0 wt. %, based on the weight of said unrefined edible oil or fat.

14. The method of claim 13 wherein said unrefined edible oil or fat is contacted with said magnesium silicate in an amount of from about 0.05 wt. % to about 1.0 wt. %, based on the weight of said unrefined edible oil or fat.

15. The method of claim 1 wherein phosphorus-containing compounds are removed from said unrefined edible oil or fat.

16. The method of claim 1 wherein soap is removed from said unrefined edible oil or fat.

17. The method of claim 1 wherein metals are removed from said unrefined edible oil or fat.

18. The method of claim 1 wherein chlorophyll is removed from said unrefined edible oil or fat.

19. The method of claim 1 wherein sterol glucosides are removed from said unrefined edible oil or fat.

20. A method of purifying an unrefined edible oil or fat, comprising:
   contacting said unrefined edible oil or fat with magnesium silicate and at least one organic acid.

21. The method of claim 20 wherein said unrefined edible oil or fat is contacted with said at least one organic acid prior to contacting said unrefined edible oil or fat with said magnesium silicate.

22. The method of claim 20 wherein said unrefined edible oil or fat is contacted with said at least one organic acid concurrently with contacting said unrefined edible oil or fat with said magnesium silicate.

23. The method of claim 20 wherein said unrefined edible oil or fat is contacted with said at least one organic acid subsequent to contacting said unrefined edible oil or fat with said magnesium silicate.

24. The method of claim 20 wherein said at least one organic acid is selected from the group consisting of citric acid, malic acid, and mixtures thereof.

25. The method of claim 24 wherein said at least one organic acid is citric acid.

26. The method of claim 24 wherein said at least one organic acid is malic acid.

27. The method of claim 20 wherein said magnesium silicate has a surface area of at least 300 square meters per gram.

28. The method of claim 27 wherein said magnesium silicate has a surface area of at least 400 to about 700 square meters per gram.

29. The method of claim 27 wherein said magnesium silicate has a particle size of from about 20 microns to about 175 microns.

30. The method of claim 27 wherein said magnesium silicate has a bulk density of from about 15 to about 35 pounds per cubic foot.

31. The method of claim 20 wherein said magnesium silicate is an amorphous hydrous precipitated synthetic magnesium silicate, said magnesium silicate having been treated to reduce the pH thereof to less than about 9.0.

32. The method of claim 31 wherein said magnesium silicate has a pH in a 5% slurry of from about 8.2 to about 8.9.

33. The method of claim 32 wherein said magnesium silicate has a pH in a 5% slurry of from 8.5 about to about 8.8.

34. The method of claim 20 wherein said magnesium silicate has a surface area of no more than 150 square meters per gram.

35. The method of claim 34 wherein said magnesium silicate has a surface area of no more than 50 square meters per gram to about 150 square meters per gram.

36. The method of claim 35 wherein said magnesium silicate has a mole ratio of MgO to $SiO_2$ of from about 1:3.0 to about 1:3.8 and a pH in a 5% water suspension of from about 9.5 to about 10.5.

37. The method of claim 20 wherein said magnesium silicate has a pH of from about 9.0 to about 9.5.

38. The method of claim 20 wherein said unrefined edible oil or fat is contacted with said magnesium silicate in an amount of from about 0.01 wt. % to about 5.0 wt. %, based on the weight of said unrefined edible oil or fat.

39. The method of claim 38 wherein said unrefined edible oil or fat is contacted with said magnesium silicate in an amount of from about 0.05 wt. % to about 1.0 wt. %, based on the weight of said unrefined edible oil or fat.

40. The method of claim 20 wherein phosphorus-containing compounds are removed from said unrefined edible oil or fat.

41. The method of claim 20 wherein soap is removed from said unrefined edible oil or fat.

42. The method of claim 20 wherein metals are removed from said unrefined edible oil or fat.

43. The method of claim 20 wherein chlorophyll is removed from said unrefined edible oil or fat.

44. The method of claim 20 wherein sterol glucosides are removed from said unrefined edible oil or fat.

45. The method of claim 20 wherein said at least one organic acid is in the form of an aqueous solution.

46. The method of claim 45 wherein said at least one organic acid is present in said aqueous solution in an amount of from about 10% to about 80% by weight.

47. The method of claim 46 wherein said at least one organic acid is present in said aqueous solution in an amount of about 50% by weight.

48. The method of claim 45 wherein said unrefined edible oil or fat is contacted with said aqueous solution of said at least one organic acid in an amount of from about 0.01 wt. % to about 5.0 wt. %, based on the weight of the unrefined edible oil or fat.

49. The method of claim 48 wherein said unrefined edible oil or fat is contacted with said aqueous solution of said at least one organic acid in an amount of from about 0.5 wt. % to about 4.0 wt. %, based on the weight of the unrefined edible oil or fat.

50. The method of claim 20 wherein said at least one organic acid is in the form of a solid powder.

51. The method of claim 50 wherein said unrefined edible oil or fat is contacted with said solid powder of said organic acid in an amount of from about 0.01 wt. % to about 5.0 wt. %, based on the weight of the unrefined edible oil or fat.

52. The method of claim 51 wherein said unrefined edible oil or fat is contacted with said solid powder of said organic acid in an amount of from about 0.5 wt. % to about 4.0 wt. %, based on the weight of the unrefined edible oil or fat.

* * * * *